United States Patent [19]
Conner

[11] Patent Number: 6,080,914
[45] Date of Patent: Jun. 27, 2000

[54] STRAWBERRY PROMOTERS AND GENES

[75] Inventor: Timothy W. Conner, Wildwood, Mo.

[73] Assignee: Monsanto Company, St. Louis, Mo.

[21] Appl. No.: 09/008,979

[22] Filed: Jan. 20, 1998

Related U.S. Application Data

[60] Provisional application No. 60/036,131, Jan. 21, 1997.

[51] Int. Cl.$^7$ ............................. A01H 5/00; C07H 21/04; C12N 5/14; C12N 15/82
[52] U.S. Cl. ....................... 800/298; 435/320.1; 435/419; 536/24.1; 800/286; 800/287
[58] Field of Search ......................... 536/24.1; 435/69.1, 435/320.1, 419, 468; 800/278, 287, 286, 298, 317.2, 317.3, 317.4, 312, 314

[56] References Cited

U.S. PATENT DOCUMENTS 4,943,674  7/1990  Houck et al. ........................... 800/205

FOREIGN PATENT DOCUMENTS

| 91/01373 | 2/1991 | WIPO | ............................. | C12N 15/00 |
| 95/35387 | 12/1995 | WIPO | ............................. | C12N 15/82 |
| 95/35388 | 12/1995 | WIPO | ............................. | C12N 15/82 |
| 97/27295 | 7/1997 | WIPO | ............................. | C12N 15/11 |
| 97/27308 | 7/1997 | WIPO | ............................. | C12N 15/82 |

OTHER PUBLICATIONS

Carpentar JL, et al. "Preferential expression of an alpha–tubulin gene of Arabidopsis in pollen." Plant Cell 4: 567–571, May 1992.
Lin E, et al. "Fruit developmental regulation of the kiwifruit actinidin promoter is conserved in transgenic petunia plants." Plant Mol. Biol. 23: 489–499, 1993.
Hamilton AJ, et al. "Antisense gene that inhibits synthesis of the hormone ethylene in transgenic plants." Nature 346: 284–287, Jul. 1990.
Benfey PN, et al. "The cauliflower mosaic virus 35S promoter: combinatorial regulation of transcription in plants." Science 250: 959–966, Nov. 1990.
Kim Y, et al. "A 20 nucleotide upstream element is essential for the nopaline synthase (nos) promoter activity." Plant Mol. Biol. 24: 105–117, 1994.
Deikman, J., et al., "Interaction of a DNA binding factor with the 5'–flanking region of an ethylene–responsibe fruit ripening gene from tomato," *EMBO J*, 7: 3315–3320 (1988).

Horsch, R.B. and Klee, H., "Rapid assay of foreign gene expression in leaf discs transformed by *Agrobacterium tumefaciens*: Role of T–DNA borders in the transfer process," *Proc. Natl. Acad. Sci. U.S.=A.*, 83: 4428–32 (1986).
Klee, H., et al., "Vectors for Transformation of Higher Plants," *Bio/Technology*, 3: 637–642 (1985).
Lin, et al., "Fruit developmental regulation of the kiwifruit actinidin promoter is conserved in transgenic petunia plants," *Plant Mol. Biol.*, 23: 489–499 (1993).
Rogers, S. G., et al., "Improved Vectors for Plant Transformation: Expression Cassette Vectors and New Selectable Markers," *Methods in Enzymology*, eds. Wu and Grossman, pp. 253–277, San Diego: Academic Press (1987).
Theologis, A., "One Rotten Apple Spoils the Whole Bushel: The Role of Ethylene in Fruit Ripening," *Cell*, 70: 181–184 (1992).
Nam, Y. et al, (Oct. 2, 1997) "AC AJ001444," EMBL Database.
Wilkinson, Jack Q et al. (1995) "Identification of mRNAs with enhanced expression in ripening strawberry fruit using polymerase chain reaction differential display," *Plant Molecular Biology* 27:1097–1108.

*Primary Examiner*—Lynette R. F. Smith
*Assistant Examiner*—Amy J. Nelson
*Attorney, Agent, or Firm*—Grace L. Bonner; Arnold White & Durkee

[57] ABSTRACT

Promoters and genes isolated from genomic DNA of strawberry plants are disclosed. Both the promoters and genes are capable of tissue-specific expression in transgenic plants. A plant promoter that is a nucleic acid region located upstream of the 5' end of a plant DNA structural coding sequence that is transcribed at high levels in ripening fruit tissue. This promoter region is capable of conferring high levels of transcription in ripening fruit tissue and in developing seed tissues when used as a promoter for a heterologous coding sequence in a chimeric gene. The promoter and any chimeric gene in which it may be used can be used to obtain transformed plants or plant cells. A DNA coding sequence that codes for a gene that is highly transcribed in ripening fruit tissue of *Fragaria X ananassa*. This coding sequence can be used to obtain a cDNA probe useful in obtaining analogous promoters from a homologous coding sequence in other plant species. Chimeric genes including the isolated promoter region, transformed plants containing the isolated promoter region, transformed plant cells and seeds are also disclosed.

12 Claims, No Drawings

SEQUENCE LISTING (1) GENERAL INFORMATION:

(iii) NUMBER OF SEQUENCES: 14

(2) INFORMATION FOR SEQ ID NO:1:

(i) SEQUENCE CHARACTERISTICS:
        (A) LENGTH: 648 base pairs
        (B) TYPE: nucleic acid
        (C) STRANDEDNESS: double
        (D) TOPOLOGY: linear (xi) SEQUENCE DESCRIPTION: SEQ ID NO:1:

```
TTATATATGC TGTTGTCCAT TGCATAATGT TCATGATCTT TTCGTTTTAT ATATCTAACT      60

TGAATTGCAT GCATACATAT AAATATATAT ATAACCACTT CGAGAACGTA GTACTACGTA     120

CTTGTTGAGG ATTTAAAATT AATTATTCCC GATTGAGTGC CATCTTCACT AATTAGTTAC     180

ATGACAACTA AATTAATGAG AACTTTTTAC ATGACAATAA TTGAGAGAGT TTGAGAGCGA     240

GAGGAGGGGG AAGAGATAGA TATGTCAATT GTGATATGAT CGATATGGAG TGTGTTTGTA     300

NGGATCGATT TGGTCGTCGT CGTCGTCTTG TTCTTCCACA AAAGAGAAAC GAAGTTGACA     360

TGAGAGGAGG AAATGAGGCC AACGGCCAGC CCCTCTCCTC CATCACCTCC ATTATTAAGA     420

TTCCTTCGGA ACTTTCCCCG GAGACTTGTG CTTCTCTCAT GCCTGCGCAG ACCCACCGCC     480

CCCACATACT CCTCAGCCTG CATGGGAAGT CGAAATTGCC ATCCTTCTCC TCCCCTCCCA     540

TGCATCTATA AATTGANGAG CCAAAGCAGG GCTTGAAGAT ATAGCAAGCA AAGCATTTTC     600

ATTAGTCAGA AACAAAAACC CAGTTTCAGT AAATCAATTC CGAGATCT                 648
```

(2) INFORMATION FOR SEQ ID NO:2:

(i) SEQUENCE CHARACTERISTICS:
        (A) LENGTH: 469 base pairs
        (B) TYPE: nucleic acid
        (C) STRANDEDNESS: double
        (D) TOPOLOGY: linear (xi) SEQUENCE DESCRIPTION: SEQ ID NO:2:

```
TTGCTCGGTT CTTAGTCAGC AACTCAGCAT ACAGTGAAAT CTGCTTAATT TTCATGGAGG      60

GTTATTTCGG TGTGAGAAAA GGTGCATGGA CTAAAGAGGA AGATGAACTT CTGAAACAGT     120

TCATCGAAAT TCATGGAGAA GGCAAATGGC ATCATGTTCC TCTCAAATCA GGTAGTTAAT     180

CTAAGATTAC GTACATGCTC TCACTGGAAA GTTTAGACTG CTGCTTATAT GTATGTTTAC     240

GTCTGTACTT GCAGGCTTAA ACAGATGCAG GAAGAGCTGT AGACTGAGAT GGCTGAATTA     300

TTTAAAGCCG AATATCAAGA GAGGAGAGTT TGCGGAGGAT GAAGTTCATT TGATCATCAG     360

GCTTCATAAG CTTCTAGGGA ACAGGTAATT AGAGCATCTG ATATGTTCGT TTCTGCTTAA     420

TTTCTCAGTT ACTGCTCTCT CAGGTAAAGC ATGCGTTATT TCTTCTGGA                469
```

(2) INFORMATION FOR SEQ ID NO:3:

(i) SEQUENCE CHARACTERISTICS:
        (A) LENGTH: 1260 base pairs
        (B) TYPE: nucleic acid
        (C) STRANDEDNESS: double
        (D) TOPOLOGY: linear (xi) SEQUENCE DESCRIPTION: SEQ ID NO:3:

```
GAGCTCAATT ATGAATCTCA CATGCCTTGT CAACAAATTT CTTTCACACT ATTTATGACA    60

CTGACATTGT CTCTGACCTT TGCTTGTTTT TAACATGGGC TGCATTTATT CAACTCACTA   120

CTATCTGCAC TGAAGCCCAA TTTGGCTACT TTGTTCACGC CGGTCGTACC TATTCCCAGT   180

TTGTTGCCTG TTCTAATTTC TATAAGCAGA CTATAAATAT AGCTTTCTTT TTCGGCTTTT   240

CCTTTCCCTT TCCCCTTTAG GCAGCAAACT TCTAATTTAC CCATTGGATT CTACCTCATT   300

CTGCAAAGTT AACCCAATAA AGCCTTTCAG TTGACATATT TACTAATACT TTTGTACTCG   360

GAGTCTTTCT TCTAATGAGA ACTCTTAAGT TAATGATTTT TCGGTTTATG GTTTAAAAGA   420

CCTATTTTTT TATCACATAT TAACATCTCA TCCGTTCAGT TTTTAGATCT ATATGAATAA   480

ATCAGTCATA CAAATCTCTA ACCCACATAA CTTACCATRR CACGTCGGAC AAAATCCAAG   540

GCCAGAAAAT CGTACCAAAT GTCTTCTTCT CGCTAAGGAT TTACCCAAAC AATATGTTCC   600

TTTACTCCAC AGTTTTCTAA TCCATAATT CTGGGGCACC ATATTTATTT CCCATAGGTG   660

CCTTTACCCA TTTGGACCAC ACAGTCTTAT ACATCCTTGG TACCAAAAAA ACCTACATTT   720

TAATTTCCTG CAACCACTAC TAGAGACTCA CATGCATGCC TCGGCCTCAA TCCCATTCCC   780

TTATTCCCAT TTACATCACT TCACCGGTCA ACATATCTCT GACCCTCCCA GAAAAGCATT   840

CCTTTCCCTT CTCCCATATA ATCCATCGGA AATCGGAATG TACCGATATA CAATTCCTCT   900

CATGTCTCTT TCTGGGCCCC CAAGCCCATC ACACCTTCCA CGTGTAGCCC ATCAACTCGT   960

GCATGGACCA TCCCCCACCT CTAATCCACC GTCGATCATA AATTTTCCGG TTATTACAAT  1020

CATACCAAAC ACATTCCAAC ACCGTTTTCC CAAACCCGGC CCAGCACGAC CGCATTGGAA  1080

GCCGAGCATA ATCCAGTCGC ATCAGCCACG TGTTTCTCCC TCATTGGATG CCGTCTGGCA  1140

TCCAATGAAC TGTATTTTTT TAATTTTTTT TCTTATAAAG AACCCCCGAG ACTGGCCTCT  1200

GCTTTGCTCT ATGTATCCTT CACCAGCAAA AACGAGAGAG AGAGAAAAAA ATGGCGCGAA  1260
```

(2) INFORMATION FOR SEQ ID NO:4:

(i) SEQUENCE CHARACTERISTICS:
        (A) LENGTH: 248 base pairs
        (B) TYPE: nucleic acid
        (C) STRANDEDNESS: double
        (D) TOPOLOGY: linear (xi) SEQUENCE DESCRIPTION: SEQ ID NO:4:

```
ATGTCGTCTT CCACGTCAGC CTGAAATGAA CCACGACTAA TATAACTAAA TTATTCGATT    60

CTATTGTCAT GCTGGTTTCG ACTGCTTCTC CACAATATAT GAGCTCTGAG CTACTCCTCT   120

CTCCAATCCC ACCACTCTCC ACTCCTCCTC TCCACTCCTC AAAGGTCTCA CCCTTTTCTC   180

TTCCGGTGGA TTATCAGAAT TTAGCTGATA AACCATCCGA CATTGCATGA TATGACCAGT   240

GTTTTAGT                                                           248
```

(2) INFORMATION FOR SEQ ID NO:5:

(i) SEQUENCE CHARACTERISTICS:
        (A) LENGTH: 552 base pairs (B) TYPE: nucleic acid
    (C) STRANDEDNESS: double
    (D) TOPOLOGY: linear (xi) SEQUENCE DESCRIPTION: SEQ ID NO:5:

| | | | | | |
|---|---|---|---|---|---|
| ATAGCAAGCA | AAGCATTTTC | ATTAGTCAGA | AACAAAAACC | CAGTTTCAGT | AAATCAATTC | 60 |
| CGATCAACAC | CATGTCTGGA | AAGTGCGACA | CGTGTGACTG | CTCTGACGTT | TCCCAGTGCA | 120 |
| CGAAGAAGGG | AAACAGCTTG | GTCATTGTTG | AGACTGAGAA | GAGCTACGAC | ACTGTTGTCA | 180 |
| TGGATGCACC | AGCCGCCGAG | AACGGCACGA | GTGCAAATGC | GGCACCACCT | GCTCTTGCAT | 240 |
| CGACTGCAAG | TGTGGACATT | AGTCCCTATT | CGACAACCAA | TGGCTGCCAT | ATAATTATTA | 300 |
| CCTAGTGATG | ATAGGAAAAG | AAAGGAGTCT | CGTCAATAAA | GGATTTGTGA | GAATCAAATA | 360 |
| ACGTACTCTG | TTTATTAATT | TGTGATAGTA | GTTTGATCGA | GTCTGTGAGT | AAGTGATCGA | 420 |
| GTAAGAGATG | TACTCTACTC | TGTGTGTGTG | TCAATCATGT | TCGTGTTCTT | TGGTAGCCAT | 480 |
| GTAATGTTCT | CCATCTGGTC | ATTATCTGTG | GCCTTGTGAT | CATGTTTAAT | CAATGAAACT | 540 |
| ACTATTAGTA | AT | | | | | 552 |

(2) INFORMATION FOR SEQ ID NO:6:

(i) SEQUENCE CHARACTERISTICS:
        (A) LENGTH: 785 base pairs
        (B) TYPE: nucleic acid
        (C) STRANDEDNESS: double
        (D) TOPOLOGY: linear (xi) SEQUENCE DESCRIPTION: SEQ ID NO:6:

| | | | | | |
|---|---|---|---|---|---|
| GGTTGATTTG | ATCATCAGGC | TTCATAAGCT | TCTAGGAAAC | AGGTGGTCTT | TAATTGCCGG | 60 |
| ACGATTGCCA | GGAAGAACTG | CCAATGATGT | GAAGAACTAT | TGGAATACTT | ATCAAAGGAA | 120 |
| AAAGGATCAA | AAGACGGCTT | CATACGCAAA | GAAACTGAAA | GTTAAACCCC | GAGAAAATAC | 180 |
| AATAGCTTAC | ACAATTGTAA | GACCTCGACC | ACGAATCCTT | CATCAAAAGG | TTCAATTTTA | 240 |
| CGGAGAGATA | TGAAAATATA | GAGCATAATC | ATTCAGAAAT | GAGTTATACC | AGTTCTTTAC | 300 |
| CAACAGCACC | ACCACAGACT | CTACTAATTA | GAAAATGTAA | CTGATTGGTG | GAAAGATTTC | 360 |
| TCAGAAGATA | GTACAGAGAG | CAATTGATAG | AACAATGTGT | TCTGGTCTTG | GTTTAGAGGA | 420 |
| TCATGACTTC | TTCACAAACT | TTTGGGTTGA | AGATATGGTA | CTATCGGCAA | GCAATCATCT | 480 |
| AGTCAACATC | TCCTACGTGT | GACTTCTTTA | AGTCTTCCTG | GTGCATATTA | GTAGTTGGTC | 540 |
| TTCTTGATTT | TTTTTTTTTC | TCTTTATTTG | GTTTCTGTAT | GTATCTGGTT | GTGCACTAGC | 600 |
| TACTAGTAGG | TTTCTATTGT | ATTTTNNNNN | AGATGACGTT | ATTTGATTCT | CACAAATCCT | 660 |
| TTATTGACGA | GACTCCTTTC | TTTTTTCCTT | ATCATCACTA | GGTAATAATT | ATATGGCAGC | 720 |
| CTTGGTTGTC | GAATAGGGGA | CTTAATTTCC | ACACTTGCAG | TCGATGCAAG | AGCAGGTGGT | 780 |
| GCCGC | | | | | | 785 |

(2) INFORMATION FOR SEQ ID NO:7:

(i) SEQUENCE CHARACTERISTICS:
        (A) LENGTH: 3981 base pairs
        (B) TYPE: nucleic acid
        (C) STRANDEDNESS: double
        (D) TOPOLOGY: linear (xi) SEQUENCE DESCRIPTION: SEQ ID NO:7:

| | | | | | |
|---|---|---|---|---|---|
| ATGGCGCGAA | ATGGCCTTTG | CTTACCGGGA | AATGTTCCCG | CATTTCGCGC | AACACTCGTC | 60 |
| CTCTCGCTGC | TCCTGCTTCT | CCAGCCAATC | AGCGCCGGCC | ACGACTACCA | CGACGCCCTC | 120 |

```
CGCAAGAGCA TCCTCTTCTT CGAAGGCCAG CGCTCCGGCA ACGTCCCGCC CGATCAACGC    180

CTCAAATGGC GCCGCGACTC CGCATTGCAC GACGGCTCCA CCGCCGGCGT AAGCTACTCT    240

CCCTCCCTCA TCTAATACAT TCAAAGTTGC TTTCAATCAA AAAGGGTTGT GGTACTCAAA    300

AAGTTGTGTG TTAAACTGCT AATATTTTAG ACTCACATTT TGTTTGTTTA TCAGGTAGAC    360

TTAACCGGCG GCTACTACGA CGCCGGCGAC AACGTGAAGT TCGGGTTTCC GATGGCGTTC    420

ACGACCACTC TGCTGGCGTG GAGCATTATA GACTTCGGGA GGGTCATGGG GACGGAGCAG    480

AGGAACGCCG TCAAGCGCTT ACGGTGGGGG ACAGACTACC TTCTGAAGGC GACGGCGGTT    540

CCCGGCGTCG TCTTCGTCCA AGCTGGCGAC CCATACTCCG ACCACAACTG CTGGGAGAGG    600

CCGGAAGACA TGGACACACG CCGCACGGTG TACAAAATCG ACCACAACAA CCCGGGATCC    660

GACGTGGCAG GCGAAACCGC CGCCGCGCTC GCCGCTGCCT CCATCGTTTT CAGGTCACGT    720

GACCCCGCTT ACTCGAGACT GCTTCTCAAT CGAGCCGTTA AGGTACGTCA CTGTCACACT    780

GATTCAATGA CTTTAATTTT TTTAACCTCG GTTGGGAAAT AGTGAAAATA GTGAAACTGA    840

CCGTTGATAC TTTCCCCCTA GGTTTTCGAG TTCGCTGATA CCCACCGCGG CGCGTACAGC    900

TCCAGCCTCA AAAACGCCGT GTGCCCTTTT TACTGCGACG TGAACGGCTT CCAGGTTAGT    960

CACCTGCAGT CTGATATTAA CTCTAGCCGT TGGATTTGTT TTAGGGTTAA TTTAACATGC   1020

GTGTATGTGC AGGATGAGTT ACTGTGGGGA GCAGCGTGGT TGCACAAGGC GTCGAGAAGG   1080

CGGCAGTACA GAGAATACAT AGTGAGAAAC GAGGTCGTTT TGAGAGCTGG AGATACCATT   1140

AACGAGTTTG GTTGGGATAA CAAGCATGCT GGGATTAATA TTCTCATTTC TAAGGTAATT   1200

AAGCTAATCC CTAACTTAGT TTGTTAATAT AATCCACTCT TAATCATTGC CTCGATTCGG   1260

GTTCTTGGTT CTTTTTGTCC TCGTGTTTTT GTTCGGAATG TGACAACTGT TCTTTACTAA   1320

TCGTATTTAG CTAGATCTTA TAACTTTGTT ATGTGCGCTT CACGTGCATA TAAAATACGA   1380

TTGTTCATTT TTGCCATGGC CGTGACACTT GAATGATTTT CTTTGCATGT GGTGCACCAT   1440

ATAGTATAGT ATTTTGGACC CAACTTGATA TCAGGTTAGA GAATAGAGAT GCTTAATTAA   1500

AGATTTTTTT TTAACTGGGG TGTACATTGT ACATGGTTGT GTCTTTCCGT ACATCTAAGA   1560

TCAATGAGAA TAATATCTGA GCTGTGTGCT AAGTAAACAA AGGAAAAGGA TTGGTCAGGA   1620

TTAGTTAGGT GGTGTAAAGT TCAAAAATAA TGATAATAGT CTACAAAATT GATGGCAAAG   1680

GTTCAATAAT CCGAGATCAA GAATGTGTTT CGTGTAACTT TGTTGAAGTA AAACTTCTCT   1740

CCTGTTCATA TACTTCGTTA AAAGTTCGGT CAAGGCTCTT GTGATAATCC GAGCTTCAAG   1800

AATGTGTTTC GTGCAATTTT GTTGCAGAAA AACTTCGCTA GTTTCTGTCC GTGAAATTGG   1860

TTAAGGGTAT CTTGTTAGAA CTGGATTGGC CTTAGAATTA GGCTTTCTGG GACTTATGGT   1920

GCGTCCATGG ATTTTGCCGT CGTTTCAATC AGAAAAAGCA AAGTGTTGGT CCAGGTCTCG   1980

AGCTCCATCT TTAGGTCTCG TGGGTCCTTA AAATAAGTGA GAGTCACTGC TACCTGCATG   2040

TGCTTAAAGA ACGACGATGG GGTTCGTCTC CCATGCCTTT TATCCTCATT CAGTCTCCCT   2100

CTACCCATTC TTAAGAAATA AGCTTTTCCC AAACCGAGTG TGACCCCGGT AAGGCTTTTC   2160

ACTACCACGA CGACGACGTT TCAATATTCC GCAATATCTT GTTTAGTATC TGAAATTCCT   2220

GAACTAGGTG TAAGAACATT ATTGAGTTAT AAAAAAATAA GATTATCTTG ATTCATGAAA   2280

ATATGAATTT CATTGGGTAA GGTACTGATA CATATTTTTC TGGGTTTTAT AAATATTGTT   2340

CGGCAGGAAG TGCTTATGGG AAAAGCAGAT TATTTCGAAT CTTTCAAGCA AAATGCAGAT   2400

GGATTTATAT GCTCTGTTTT GCCTGGACTT GCCCATACCC AAGTCCAATA TTCTCCAGGT   2460
```

```
                              -continued

ATATTTTCAG CTTCTTTTTT TTTTTCCTTA TTTTCGAAAA TAAAGAATTA GAATTAGGGT    2520

TGCTTCTTTC TCAAAACGAG AAAAATAAGA ATTAGGGTTT GCTTTACTTG CTGAATAATT    2580

TTTCTGATTA GGGTTCTTTG TTTTGAAGGT GGTTTGATCT TCAAGCCTGG AGGGAGTAAC    2640

ATGCAGCATG TAACTTCGCT CTCGTTCCTA CTTTTGACTT ATTCCAACTA TATAAGCCAC    2700

GCCAATAAGA ACGTGCCGTG TGGCATGACC TCCGCCTCCC CGGTCTTCCT CAAACAATTG    2760

GCTAAACGCC AGGTAACTTT ATCACAACCC ACCAACATCC AATGAAACCC TACAAAGACT    2820

ACAGTTCTAG GGCTACTATT CCCTGTTTCT CATTAATTCA TGCAATCATG GACCACTTCT    2880

CCTTCAGACA AATTAACGGC TAGATTTTAT CCTTGTCTCA CCTTACCTTA ACTCGCTGCC    2940

ACATTGTACT TTTGTTCACA CACAAAATCT ATGAAGATTG TCCACATTAT TGCTTGACCT    3000

AATGACCTAT ATGCTCAAGC ATCCAAGGAC AGGGGTGGTT ATGGAAATAT GTTCAAGTTT    3060

TAGGATAGTA GTGTAATTAT TGAACTTGTG TTTTTGCAGG TGGACTACAT TTTGGGTGAC    3120

AATCCATTGA GAATGTCTTA CATGGTTGGA TATGGGCCGC GTTACCCGCA GAGGATTCAC    3180

CACCGGGGCA GCTCACTTCC ATCTGTGCAG GCCCATCCAG CCCGTATCAG ATGCAAAGCC    3240

GGTTCTCGTT ATTTTCTGAG TCCGAATCCA AACCCGAATA AACTAGTTGG GGCGGTTGTG    3300

GGCGGACCTA ATAGCTCGGA TGCATTTCCG GACTCTAGGC CTTACTTTCA AGAGTCCGAA    3360

CCCACGACGT ACATAAATGC GCCGCTTGTG GGCCTACTTT CGTATTTTGC AACCCATTAC    3420

TGATTCTCGA AGTGTAAACA GTGAATGAGA ATTTGTAGTG GTGCGCCAAT AGTCACCCAC    3480

CAATCCCCCA CTCTACCAAT TGTTGTTACT CGTAAGGTTC TAATTGTTAA TTTCTATCAA    3540

TGAAGTCATG AAGAAAGAAA ATGGGCCAGG CTTAGTTATG GAATTTAGTC TCAGAAGCCC    3600

GACTGTTGTT ACTTTTGCAA GGTACTAGTT GTATCAATAT TTCTGTCAAC AAAGAAAGAA    3660

AATGGGCCAA GCCTAGATGC GGAATTTTGT CTCAAAATTC CTAGCTAGTT TTGTGTCTCC    3720

TTGTTTGATC TAATAATTTA CTTGGTCTTT CGAGAACCTA ATGTCAAAAT TGAACTGATG    3780

TAGATTGAAA GCAGAAATAA CCGAGAGAGG GAGTCTATTT TCCTAACATG TGTGTGCATG    3840

AGAGGAGTGT CCTAGCGAGG TCACCGCATC AACCACAAAG TTCACATCCC TAAGGACATG    3900

CCGGTCGGAG ATATGTTCAA AAAGATCCGA ATTCTTCGCC CTATAGTGAG TCGTATTGAC    3960

GGCCGCGTCG ACAGCTCTAG A                                              3981

(2) INFORMATION FOR SEQ ID NO:8:

(i) SEQUENCE CHARACTERISTICS:
        (A) LENGTH: 752 base pairs
        (B) TYPE: nucleic acid
        (C) STRANDEDNESS: double
        (D) TOPOLOGY: linear (xi) SEQUENCE DESCRIPTION: SEQ ID NO:8:

ATGGAGAAAT TTGTGAGACT CGTTTCCTTG GCTCCTCTGT TTCTGCTTCT CTGTTTTCCT      60

CTGGCTCTGG CTGGTCATGA CTATGGCGCA GCTCTCAGCA AGAGCATTCT CTTCTTTGAA     120

GCTCAGAGAT CTGGTGTCCT TCCCCATAAC CAAAGGGTCA CTTGGAGATC CCACTCCGGT     180

TATACGATGC AAAGCCAGCG GGGTGAGTCA TTTGTGTTAT GTTTTTACTG TCAAAATTTA     240

CAGTTCCCAG CCCTGATACT TATAGATTGA TTTCGGTGGT GCAATTTGGT CTGAACTTGT     300

TTGAATCTGT AGGTGAACCT TGTTGGGGGC TACTATGACG CAGGGGACAA TGTGAAATTC     360

GGGCTTCCGA TGGCGTTCAC TGTTACAATG ATGTCCTGGA GTATAATAGA GTATGGAAAG     420

CAAATGGCTT CAAGCGGTGA ACTTCTTGGG CACGCCTTGG ACGCTGTTAA GTGGGGAACT     480
```

```
GACTACTTCA TTAAGGCTCA CCCAGAACCC AACGTTCTCT ATGGAGAGGT AGCTTTCAAC      540

TCAAAACACT AACAGAACCA TTTTTCTAAT AACCCTTTCA GTCACTTCAA AAAGCTCTCT      600

ACTTGGTTAC CATCACTTTG AAAAAGATCT CCAAGTTTCT ATTCTTTATT GACTAATCTA      660

TCTTTTTTTC TACACGGGAT TGTTTTATT TAATTATATA AAAACGAAAC GAAACCCAAA       720

TTGGCAAAAG TAATATCATT GTTTATTGAT GA                                    752

(2) INFORMATION FOR SEQ ID NO:9:

(i) SEQUENCE CHARACTERISTICS:
        (A) LENGTH: 39 base pairs
        (B) TYPE: nucleic acid
        (C) STRANDEDNESS: single
        (D) TOPOLOGY: linear (xi) SEQUENCE DESCRIPTION: SEQ ID NO:9:

GTAAATCAAT TCCGAGATCT ACCATGGCTG GAAAGTGCG                              39

(2) INFORMATION FOR SEQ ID NO:10:

(i) SEQUENCE CHARACTERISTICS:
        (A) LENGTH: 39 base pairs
        (B) TYPE: nucleic acid
        (C) STRANDEDNESS: single
        (D) TOPOLOGY: linear (xi) SEQUENCE DESCRIPTION: SEQ ID NO:10:

TTAGACTGCT GAGATCTACC ATGGTTACGT CTGTACTTG                              39

(2) INFORMATION FOR SEQ ID NO:11:

(i) SEQUENCE CHARACTERISTICS:
        (A) LENGTH: 35 base pairs
        (B) TYPE: nucleic acid
        (C) STRANDEDNESS: single
        (D) TOPOLOGY: linear (xi) SEQUENCE DESCRIPTION: SEQ ID NO:11:

ACGAGAGAGA GAGAAAACCA TGGCGCGAAA TGGCC                                  35

(2) INFORMATION FOR SEQ ID NO:12:

(i) SEQUENCE CHARACTERISTICS:
        (A) LENGTH: 35 base pairs
        (B) TYPE: nucleic acid
        (C) STRANDEDNESS: single
        (D) TOPOLOGY: linear (xi) SEQUENCE DESCRIPTION: SEQ ID NO:12:

CACAAATTTC TCCATGGTGG ATCCCTGGTC ATATC                                  35

(2) INFORMATION FOR SEQ ID NO:13:

(i) SEQUENCE CHARACTERISTICS:
        (A) LENGTH: 31 base pairs
        (B) TYPE: nucleic acid
        (C) STRANDEDNESS: single
        (D) TOPOLOGY: linear (xi) SEQUENCE DESCRIPTION: SEQ ID NO:13:

CAAAGCTTGG NTAYTAYGAY GCNGGNGAYA A                                      31

(2) INFORMATION FOR SEQ ID NO:14:

(i) SEQUENCE CHARACTERISTICS:
```

-continued

```
  (A) LENGTH: 34 base pairs
  (B) TYPE: nucleic acid
  (C) STRANDEDNESS: single
  (D) TOPOLOGY: linear (xi) SEQUENCE DESCRIPTION: SEQ ID NO:14:

TCGAATTCTC CATRTCYTCN GGNCKYTCCC ARCA                                   34
```

STRAWBERRY PROMOTERS AND GENES

This application claims priority from U.S. Provisional Application Ser. No. 60/036,131, filed Jan. 21, 1997.

FIELD OF THE INVENTION

The present invention relates to plant genetic engineering and more specifically to novel plant genes and selective gene expression in plants. In particular, the present invention relates to novel promoters capable of conferring high levels of transcription of heterologous genes in cells of fruit tissue, novel chimeric genes selectively expressed in cells of fruit, and transformed plants containing said chimeric genes.

BACKGROUND OF THE INVENTION

One of the goals of plant genetic engineering is to obtain plants having improved characteristics or traits. Many different types of characteristics or traits in plants are considered advantageous. Those of particular importance with regard to fruit bearing plants include control of fruit ripening, improvements in the nutritional characteristics of the edible portions thereof, resistance to plant diseases, resistance to insects, cold tolerance and enhanced stability or shelf-life of the ultimate consumer product obtained from the plant.

At least two key components are required to stably engineer a desired trait, or control of such a trait, into a plant. The first key component comprises identifying and isolating the gene(s) which either encode(s) or regulate(s) a particular trait. The second component comprises identifying and isolating the genetic element(s) essential for the actual expression and/or selective control of the newly isolated gene(s) so that the plant will manifest the desired trait and, ideally, manifest the trait in a controlled or controllable manner. This second component, which controls or regulates gene expression, typically comprises transcriptional control elements known as promoters. Although a generic class of promoters which drive the expression of heterologous genes in plants have been identified, a broad variety of promoters active in specific target tissues or cells of plants remain to be described. The identification of such target or tissue-specific promoters is critical to the introduction of the above-mentioned tissue-specific improvements in plants such as fruit bearing plants.

Several promoters useful in expressing heterologous genes in selected fruits have already been identified. For example, the E4 and D8 promoters (Deikman, et al.), the kiwifruit actinidin promoter (Lin, et al.) and promoter for polygalacturonase are known to be fruit specific. U.S. Pat. No. 4,943,674 (Houck et al., Jul. 24, 1990) discloses a 2A11 promoter as useful in expression of a heterologous gene in tomato fruit. These promoters, however, have been isolated from fruit tissue which comprises mature or maturing ovaries (hereinafter referred to as "traditional fruit"). As such, these traditional fruit promoters would be ineffective in controlling desired traits in such accessory fruit bearing plants as strawberry, apple, pear, quince and the like wherein the major portion of the edible fruit comprises receptacle tissue (see *An Introduction to Plant Biology.* 2nd Edition, Braungart & Arnett, eds., C. V. Mosby Co. 1965). Similarly, to date, genes thought to be active in fruit tissue have been isolated from traditional fruit tissue instead of receptacle containing tissue.

There exists a need for receptacle tissue selective promoters in the art. Access to receptacle tissue selective promoters would enable the genetic engineering of fruit tissue from commercially important plants such as strawberry, apple, and pear. Screening of DNA libraries was undertaken as a method for the identification of tissue selective promoters from strawberry. Four such sequences were identified, and the promoters and their associated structural genes sequenced. Expression of reporter genes in tobacco and tomato plants was used as an assay of the tissue specificity of the isolated promoters. Methods for the identification and isolation of analogous promoters and structural genes from other plants is described.

SUMMARY OF THE INVENTION

The present invention provides novel promoters termed "GSRE2, GSRE49, SEL1, and SEL2" herein which cause tissue-specific expression of heterologous DNA in the receptacle tissue of plants.

The present invention also provides novel chimeric genes comprising a receptacle tissue-specific promoter operably coupled to a heterologous DNA sequence.

The present invention further provides novel genes which are highly expressed in ripening receptacle tissue of accessory fruit plants.

The present invention furthermore provides a method for expression of a heterologous gene, the improvement which comprises the use of an accessory fruit plant promoter which causes tissue-specific expression in seed, sink and receptacle tissue of plants, said accessory fruit plant promoter having a sequence selected from the group consisting of those sequences shown in SEQ ID NOS. 1, 2, 3, and 4 and sequences substantially homologous thereto.

The present invention further provides structural DNA sequences transcribed at high levels in the receptacle tissue of fruit bearing plants, the structural DNA sequences having a sequence selected from the group consisting of those shown in SEQ ID NOS. 5, 6, 7, and 8 and sequences substantially homologous thereto.

Novel transformed plant cells and transgenic plants comprising the heterologous genes of the present invention or produced by the methods of the present invention are additionally provided.

DEFINITIONS

The following definitions are provided as an aid to understanding the detailed description of the present invention.

The phrases "coding sequence" and "structural sequence" refer to the region of continuous sequential DNA triplets encoding a protein, polypeptide, or peptide sequence.

The phrase "DNA segment heterologous to the promoter region" means that the coding DNA sequence does not exist in nature in the same gene with the promoter to which it is now attached.

The phrase "expressibly coupled" and "expressibly linked" refer to a promoter or promoter region and a coding or structural sequence in such an orientation and distance that transcription of the coding or structural sequence may be directed by the promoter or promoter region.

The term "expression" refers to the transcription of a gene to produce the corresponding mRNA and translation of this mRNA to produce the corresponding gene product, i.e., a peptide, polypeptide, or protein.

The term "expression of antisense RNA" refers to the transcription of a DNA to produce an first RNA molecule capable of hybridizing to a second RNA molecule encoding a gene product, e.g. a protein. Formation of the RNA-RNA hybrid inhibits translation of the second RNA molecule to produce the gene product.

The term "gene" refers to chromosomal DNA, plasmid DNA, cDNA, synthetic DNA, or other DNA that encodes a peptide, polypeptide, protein, or RNA molecule, and regions flanking the coding sequence involved in the regulation of expression.

"Homology" refers to the level of similarity between nucleic acid or amino acid sequences in terms of percent nucleotide or amino acid positional identity, respectively, i.e., sequence similarity or identity. Note Reeck et al. *Cell* 50: 667 (1987) in this regard. Homology also refers to the concept of similar functional properties among different nucleic acids or proteins.

"Hybridization" refers to the ability of a strand of nucleic acid to join with a complementary strand via base pairing. Hybridization occurs when complementary sequences in the two nucleic acid strands bind to one another.

"Overexpression" refers to the expression of a polypeptide or protein encoded by a DNA introduced into a host cell, wherein said polypeptide or protein is either not normally present in the host cell, or wherein said polypeptide or protein is present in said host cell at a higher level than that normally expressed from the endogenous gene encoding said polypeptide or protein.

The term "promoter" or "promoter region" refers to a DNA sequence, usually found upstream (5') to a coding sequence, that controls expression of the coding sequence by controlling production of messenger RNA (mRNA) by providing the recognition site for RNA polymerase and/or other factors necessary for start of transcription at the correct site. As contemplated herein, a promoter or promoter region includes variations of promoters derived by means of ligation to various regulatory sequences, random or controlled mutagenesis, and addition or duplication of enhancer sequences. The promoter region disclosed herein, and biologically functional equivalents thereof, are responsible for driving the transcription of coding sequences under their control when introduced into a host as part of a suitable recombinant vector, as demonstrated by its ability to produce mRNA.

The term "receptacle tissue" refers to the fruit tissues of plants.

As used herein, the term "receptacle tissue-specific" when applied to a promoter, gene, structural DNA sequence or protein means having a higher level of activity in receptacle tissue of a plant relative to its level of activity in other tissues of a plant.

The term "recombinant DNA construct" or "recombinant vector" refers to any agent such as a plasmid, cosmid, virus, autonomously replicating sequence, phage, or linear or circular single-stranded or double-stranded DNA or RNA nucleotide sequence, derived from any source, capable of genomic integration or autonomous replication, comprising a DNA molecule in which one or more DNA sequences have been linked in a functionally operative manner. Such recombinant DNA constructs or vectors are capable of introducing a 5' regulatory sequence or promoter region and a DNA sequence for a selected gene product into a cell in such a manner that the DNA sequence is transcribed into a functional mRNA which is translated and therefore expressed. Recombinant DNA constructs or recombinant vectors may be constructed to be capable of expressing antisense RNAs, in order to inhibit translation of a specific RNA of interest.

"Regulatory sequence" refers to a nucleotide sequence located upstream (5'), within, and/or downstream (3') to a DNA sequence encoding a selected gene product whose transcription and expression is controlled by the regulatory sequence in conjunction with the protein synthetic apparatus of the cell.

The term "substantially homologous" refers to two sequences which are at least 90% identical in sequence.

"Transformation" refers to the introduction of DNA into a recipient host or hosts. "Host" or "hosts" refers to bacteria, entire plants, plantlets, or plant parts such as plant cells, protoplasts, calli, roots, tubers, propagules, seeds, seedlings, pollen, and plant tissues.

DETAILED DESCRIPTION OF THE PREFERRED EMBODIMENTS

The present invention provides structural DNA sequences and their promoters, which are active in the receptacle tissue of plants, and in particular, accessory fruit bearing plants. The novel genes, DNA sequences and promoters of the present invention now provide an opportunity to engineer agriculturally and commercially important traits into a new class of fruits, fruit tissue and fruit bearing plants. More specifically, the new class of fruits includes those plants comprising accessory fruit and other plants in which regulation of receptacle function or engineered expression in receptacle tissue is desirable.

In one embodiment, DNA sequences, genes and promoters are provided which are active in strawberry plants. Strawberry plants are an important commercial fruit crop in many temperate regions of the world and are especially suitable for improvement through genetic engineering techniques, such as clonal propagation, versus conventional breeding and selection. The high heterozygosity and polyploidy associated with commercial lines of strawberry plants hinder the improvement of such plants through traditional breeding methods. In contrast, clonal propagation of strawberry plants provides for stable transformation of a single dominant gene for a desired trait into a commercially important genotype without sexual recombination. The novel promoters and genes of the present invention now provide an opportunity to engineer into such receptacle fruit bearing plants as strawberry such commercially and agriculturally desirable traits including delayed fruit ripening, increased sugar content, modified color and fungal resistance as more specifically described hereinafter.

In one important embodiment of the present invention, four distinct, novel promoters, each individually able to direct high level transcription of a second DNA sequence expressively coupled thereto in ripening receptacle tissue of accessory fruit bearing plants, are provided. These promoters are designated GSRE2, GSRE49, SEL1, and SEL2. Nucleotide sequences of these promoters are provided in SEQ ID NOS. 1, 2, 3, and 4, respectively. It is understood by those of ordinary skill in the art that the DNA sequences shown in any of SEQ ID NOS. 1, 2, 3, and 4, include any promoter active in ripening receptacle tissue having a DNA sequence substantially homologous to any one of said promoter sequences.

Novel fruit specific promoters exhibiting high and specific expression during the development of the strawberry fruit have been isolated. A differential screening approach utilizing a strawberry fruit cDNA library was used to identify suitable cDNA clones that expressed specifically in receptacle tissues. cDNA probes, prepared from mRNA extracted from fruit were used.

Clones that expressed abundantly in the ripening receptacle tissue of accessory fruit plants and that showed no detectable expression in leaf tissues were identified. The low number of clones isolated, and the lack of sequence variability indicated a low gene copy number. The promoters for these cDNA clones were then isolated by the screening of a genomic DNA library. The expression of these promoters was confirmed by fusion to the β-glucuronidase (GUS) gene and following the expression of the GUS enzyme during development in transgenic fruit. Results are given below in Example 3.

The promoters of the present invention may be used to increase the sugar content in fruit. In particular, one may inhibit the action of the plant glucose-6-phosphatase gene by controlling transcription of an antisense sequence corresponding to one or both of the subunits of glucose-6-phosphatase.

Other genes which might be usefully fused to a promoter of the present invention include sucrose phosphate synthase (SPS), which is thought to control the overall rate of sucrose biosynthesis in plant cells. Expression of an SPS gene, driven by GSRE2, GSRE49, SEL1, or SEL2 may result in a developing fruit with higher carbohydrate composition.

Another possible use is with the invertase gene. Expression of invertase in a sink cell such as in a fruit is a method for increasing the ability of a cell to act as a stronger sink by breaking down sucrose to metabolites that can be used in carbon utilization pathways, e.g., starch biosynthesis. More sucrose is then mobilized into the sink tissue. Expression of invertase in the proper tissue and cellular compartments when the fruit is a strong sink, i.e., in a green fruit, is highly desirable.

Lastly, the use of promoters of the present invention with a gene for sucrose synthase would be desirable for the reasons given for the SPS.

Plant Transformation/Regeneration

A double-stranded DNA molecule containing one of the promoters of the present invention can be inserted into the genome of a plant by any suitable method. Suitable plant transformation vectors include those derived from a Ti plasmid of *Agrobacterium tumefaciens*, as well as those disclosed, e.g., by Herrera-Estrella, L., et al., Klee, H. J., et al., and EPO publication 120,516 (Schilperoort et al.). In addition to plant transformation vectors derived from the Ti or root-inducing (Ri) plasmids of Agrobacterium, alternative methods can be used to insert the DNA constructs of this invention into plant cells. Such methods may involve, for example, the use of liposomes, electroporation, chemicals that increase free DNA uptake, free DNA delivery via microprojectile bombardment, and transformation using viruses or pollen.

A particularly useful Agrobacterium-based plant transformation vector for use in transformation of strawberry plants is plasmid vector pMON505 (Rogers, S. G. et al.). Binary vector pMON505 is a derivative of pMON200 in which the Ti plasmid homology region, LIH, has been replaced with a 3.8 kb HindIII to SmaI segment of the mini RK2 plasmid, pTJS75 (Schmidhauser, T. J. and Helinski, D. R.). This segment contains the RK2 origin of replication, oriV, and the origin of transfer, oriT, for conjugation into Agrobacterium using the tri-parental mating procedure (Horsch, R. B. and Klee, H.). Plasmid pMON505 retains all the important features of pMON200 including the synthetic multi-linker for insertion of desired DNA fragments, the chimeric NOS/NPTII'/NOS gene for kanamycin resistance in plant cells, the spectinomycin/streptomycin resistance determinant for selection in *Escherichia coli* and *Agrobacterium tumefaciens*, an intact nopaline synthase gene for facile scoring of transformants and inheritance in progeny and a pBR322 origin of replication for ease in making large amounts of the vector in *Escherichia coli*. Plasmid pMON505 contains a single T-DNA border derived from the right end of the pTiT37 nopaline-type T-DNA. Southern analyses have shown that plasmid pMON505 and any DNA that it carries are integrated into the plant genome, that is, the entire plasmid is the T-DNA that is inserted into the plant genome. One end of the integrated DNA is located between the right border sequence and the nopaline synthase gene and the other end is between the border sequence and the pBR322 sequences.

Another particularly useful Ti plasmid cassette vector is pMON17227. This vector is described by Barry et al. in WO 92/04449 and contains a gene encoding an enzyme conferring glyphosate resistance which is an excellent selection marker gene for many plants.

When adequate numbers of cells (or protoplasts) containing the gene of choice driven by a promoter of the present invention are obtained, the cells (or protoplasts) are regenerated into whole plants. Choice of methodology for the regeneration step is not critical, with suitable protocols being available for hosts from tomato and peppers.

By using the promoter sequences provided herein, one of ordinary skill in the art is now able to isolate, or chemically or enzymatically synthesize, by conventional methodologies, promoters having sequences essentially identical to those sequences described herein and promoters substantially homologous thereto. For example, the isolation of such promoter sequences can be achieved by using conventional techniques to synthesize a hybridization probe comprising all or a portion of a promoter sequence set forth in any of SEQ ID NOS. 1, 2, 3, and 4. The hybridization probe is preferably about 20 to 600 nucleotides in length.

The probe is then employed to screen genomic DNA libraries created from fruit, leaves and/or roots or flowers, made from receptacle fruit bearing plants such as strawberry.

In one specific embodiment of the present invention, essentially identical or substantially homologous receptacle tissue-specific promoter sequences are isolated from a genomic library created from *Fragaria X ananassa* DNA. Specifically, a probe is hybridized to *Fragaria X ananassa* genomic DNA fragments under medium to high stringency hybridization conditions (Maniatis et al., 1982). The identified genomic fragments are then isolated and purified. Confirmation of receptacle tissue-specific activity can then be achieved by transforming plants, or plant tissue with chimeric genes containing said substantially homologous sequences in accordance with the examples hereinafter.

In another important aspect of the present invention, the novel promoters described herein may be identified and defined by their respective locations in the genomes of accessory fruit bearing plants. Specifically, these promoters comprise nucleic acid regions located upstream of the 5' end of the plant structural DNA coding sequences of the present invention which structural DNA sequences are transcribed at high levels in ripening receptacle tissue of accessory fruit bearing plants relative to other developmental tissues and stages of accessory fruit development. Said structural DNA sequences comprise the sequences shown in SEQ ID NOS. 5, 6, 7, and 8. With the discovery and teaching herein of these structural DNA coding sequences, those of ordinary skill in the art are now able to employ said sequences to both identify and isolate substantially homologous structural DNA sequences and their respective promoters.

Unlike promoter sequences, it is well established that structural DNA sequences exhibit a high level of sequence conservation across evolutionarily related genus and species. Therefore, the structural sequences depicted in SEQ ID NOS. 5, 6, 7, and 8 enable the isolation of the class of accessory fruit promoters embodied in the present invention. Specifically, the structural DNA sequences described herein are employed to identify genes comprising the structural DNA sequence and promoter regions operably linked thereto.

In one embodiment, cDNA probes comprising all or a portion of the structural DNA sequences described in any of SEQ ID NOS. 5, 6, 7 or 8 are employed to identify and isolate homologous genes from genomic DNA libraries made from plant material. The homologous genes are then isolated and the 5' upstream promoter region is identified. Promoter sequences so isolated are considered to be within the scope of the present invention.

Adjacent upstream sequences of the coding region can be isolated using a known short sequence by inverse PCR. Several modifications of the polymerase chain reaction that allows isolation of a sequence with only one known end is possible (*PCR Technology: Current Innovations*, Griffin and Griffin eds., CRC Press, Inc., 1994). Internal sequence oligonucleotides can be synthesized to an homologous region of a structural gene or promoter sequence. A small number of PCR cycles can be performed on a reaction consisting of a DNA template (either genomic DNA or a genomic library), Taq DNA polymerase and the specific oligonucleotide probe in the appropriate reaction buffer. Once unidirectional synthesis has occurred, the DNA may be digested with enzymes further upstream of the primer, and ligated with the complementary linker, and oligonucleotides homologous to this linker sequence along with the internal oligonucleotides can be used to amplify the promoter sequence. This promoter fragment can then be cloned and used as a promoter to drive expression of a desired coding sequence.

This invention also provides a DNA coding sequence that codes for a sequence that is highly transcribed in the fruit tissue of *Fragaria X ananassa*. The coding sequence can be used to make a probe to isolate homologous coding sequences in other plant species so that the corresponding promoter region from other plant species having the same tissue-specific qualities can be isolated and used. Hence, in one aspect the present invention provides a plant promoter comprising a region of DNA located at the 5' end of a plant gene that contains a structural DNA coding sequence that is homologous to the DNA sequences as shown in SEQ ID NOS. 5, 6, 7, and 8, said region of DNA being capable of conferring high levels of transcription in fruit and sink tissues.

In one embodiment of the present invention, the genomic library may be created from strawberry plant material. More specifically, said genomic library is preferably created using conventional techniques from *Fragaria X ananassa* leaf tissue. The DNA sequences which hybridize to the probes are then isolated, sequenced and the promoter region identified. Substantially homologous DNA structural coding sequences and their respective promoters are isolated from the same or different genomic libraries by employing degenerate DNA primers modeled on the DNA structural sequences in any of SEQ ID NOS. 5, 6, 7 or 8, and then proceeding with the same basic PCR technology and screening procedure.

In another embodiment, the isolated promoter sequences of the present invention are useful in directing and/or regulating the transcription of a structural DNA coding sequence expressively coupled thereto for the purpose of expressing peptides or polypeptides involved in the control or delay of fruit ripening, fruit color or aroma, production of disease resistant factors, and improvements in the nutritional quality or content of the fruit in plants transformed therewith. Examples of such peptides or polypeptides include polygalacturonase or its subunits, pectin methylesterase, xyloglucanase or other beta-1,4-glucanases, glycosidases, beta-galactosidase, alcohol dehydrogenase or lipoxygenase and enzymes of the ethylene biosynthetic pathway (Theologis, A.). Additionally, such agents as glucose oxidase, chitinase, beta-1,3-glucanase, active in fungal resistance may be expressively coupled to one or more promoters of the present invention. Also of interest are carbohydrate-modifying genes or those known to increase carbohydrate metabolism, such as ADP glucose pyrophosphorylase.

A promoter region so isolated can be fused to a desired coding sequence and polyadenylation site to create a chimeric gene. This gene can then be transformed into a plant by several different methods. In the transformed plant, the promoter will confer high level transcription and expression of the contiguous structural coding sequence in fruit and/or sink tissues in the plant.

Similarly, in another important aspect of such coupling, a gene comprising one or more of the novel promoters described herein expressively coupled to a single or multiple copies of a novel structural DNA sequence of the present invention, is constructed and used to transform an accessory fruit plant to effect increased expression of the structural DNA sequence. The enhanced expression of the structural DNA coding sequences in the transformed plants would effectively accelerate the ripening of the fruits of said plants, thereby shortening the ripening cycle of such fruits, thereby increasing the number of harvests per growing season or, thereby allowing for a growing season not otherwise possible in, for example, a particular geographic location or area of the world. In one embodiment, a gene comprising a single promoter of the present invention is preferably constructed by expressively linking the promoter to a single structural DNA coding sequence described herein and the accessory fruit plant transformed therewith is preferably strawberry.

The linking of one such promoter sequence to a desired structural coding sequence, of either endogenous or heterologous origin, is achieved by constructing a gene, utilizing conventional recombinant techniques, having one such promoter sequence located 5' to the desired structural coding sequence. The spacing between the promoter and 5' end of the structural coding sequence should be between 10 base pairs and 250 base pairs, preferably between 40 and 80 base pairs in length. The linking of a promoter and an antisense encoding sequence is achieved in a similar manner, except with the gene being in the opposite orientation with respect to the promoter.

In order to effect such transcription, a promoter sequence is synthesized, or isolated from a genomic library and cut with appropriate restriction endonucleases to obtain a nucleotide length that it is capable of initiating and regulating transcription of a DNA structural sequence to which it is coupled. Such promoter regions are typically between 0.5 kilobase (kb) to 4 kb in length. The preferred length of the promoter region is about 1 kb.

A promoter region isolated from *Fragaria X ananassa* was operably linked to reporter genes and transformed into plant cells to test the activity of the promoter region. Any promoter region isolated pursuant to this invention can be tested in a similar manner. Transformed plants containing a promoter region that directs high levels of transcription of a heterologous gene to which it is operably linked can be obtained by standard methods known to those skilled in the art.

A typical chimeric gene to be transformed into a plant of choice will include a promoter region, a heterologous structural coding sequence and a 3' non-translated polyadenylation site. A heterologous structural coding sequence denotes a structural coding sequence that is not native to the plant being transformed or a structural coding sequence that has been engineered for improved characteristics of its protein product. Heterologous with respect to the promoter means that the coding sequence does not exist in nature in the same gene with the promoter to which it is now attached. Chimeric means a novel non-naturally occurring gene which is comprised of parts of different genes. In chimeric genes utilizing the promoter of the present invention any type of heterologous structural coding sequence can be utilized to obtain the trait or characteristic desired. The 3' non-translated region contains a polyadenylation signal which functions in plants to cause the addition of polyadenylate nucleotides to the 3' end of the viral RNA. Examples of suitable 3' regions are (a) the 3' transcribed, non-translated regions containing the polyadenylation signal of the tumor-inducing (Ti) plasmid genes of Agrobacterium, such as the nopaline synthase (NOS) gene, and (2) plant genes like the 7s soybean storage protein genes and the pea E9 small subunit of the RuBP carboxylase gene.

The RNA produced by a DNA construct of the present invention also contains a 5' non-translated leader sequence. This sequence can be derived from the promoter selected to express the gene, and can be specifically modified so as to increase translation of the mRNA. The 5' non-translated regions may also be obtained from viral RNAs, from suitable eukaryotic genes, or from a synthetic gene sequence. The present invention is not limited to constructs, as presented in the following examples, wherein the non-translated region is derived from the 5' non-translated sequence that accompanies the promoter sequence. Rather, the non-translated leader sequence can be part of the 5' end of the non-translated region of the native coding sequence for the heterologous coding sequence, or part of the promoter sequence, or can be derived from an unrelated promoter or coding sequence as discussed above. A DNA construct of the present invention can be inserted into the genome of a plant by any suitable method. Suitable plant transformation vectors include those derived from a Ti plasmid of *Agrobacterium tumefaciens*, such as those disclosed by Herrera-Estrella (1983), Bevan (1983), Klee (1985) and EPO publication 120,516 (Schilperoort, et al.). In addition to plant transformation vectors derived from the Ti or root-inducing (Ri) plasmids of Agrobacterium, alternative methods can be used to insert the DNA constructs of this invention into plant cells. Such methods may involve, for example, the use of liposomes, electroporation, chemicals that increase free DNA uptake, particle gun technology, and transformation using viruses.

The construction of vectors capable of being inserted into a plant genome via *Agrobacterium tumefaciens* mediated delivery is known to those of ordinary skill in the art. Typical plant cloning vectors comprise selectable and scoreable marker genes, T-DNA borders, cloning sites, appropriate bacterial genes to facilitate identification of transconjugates, broad host-range replication and mobilization functions and other elements as desired.

If Agrobacterium mediated delivery is chosen, once the vector has been introduced into the disarmed Agrobacterium strain, the desired plant can then be transformed. Any known method of transformation that will work with the desired plant can be utilized. These methods include the leaf disc method of Horsch et al. (1985) and as adapted by Hinchee et al. (in preparation), and James et al. (1990) for strawberry.

Suitable plants for the practice of the present invention include, but are not limited to, any sink tissue of plants including strawberry, raspberry, tomato, potato tuber, tobacco, soybean, cotton ball, and cotton seed.

The expression pattern of these promoters in strawberry fruit can be confirmed by fusion to the β-glucuronidase (GUS) gene and by following the expression of the GUS enzyme during development in transgenic fruit.

Other genes which might be usefully fused to a promoter of the present invention include sucrose phosphate synthase (SPS), which is thought to control the overall rate of sucrose biosynthesis in plant cells, and sucrose synthase. Expression of an SPS or sucrose synthase gene, driven by a promoter of the present invention, may result in a developing fruit with stronger sink activity.

Alternatively, in order to increase sucrose content in fruit, one might want to lower the level of the native plant glucose-6-phosphatase enzyme(s) by incorporating an anti-sense sequence (or a sense sequence for co-suppression) corresponding to one or both of the subunits of the native glucose-6-phosphatase.

Another possible use is with an invertase gene. Expression of invertase in a sink cell such as in a fruit is another method for increasing the ability of a cell to act as a stronger sink by breaking down sucrose to metabolites that can be used in carbon utilization pathways, e.g., starch biosynthesis. More sucrose is then mobilized into the sink tissue.

In addition, the promoters may be used to drive genes which alter the ripening characteristics of fruit, such as ACC synthase or ACC deaminase. There may be many other genes which need tissue-specific promoters of varying strengths and growth profiles, for which the promoters of the present invention would be very useful.

The embodiments described above and the following examples are provided to better elucidate the practice of the present invention. It should be understood that these embodiments and examples are provided for illustrative purposes only, and are not by way of limitation of the scope of the invention.

The following experimental protocol describes the identification and isolation of the promoter of a gene differentially expressed in the receptacle tissue of plants. One skilled in the art will recognize that substitutions and alterations may be made in the components, conditions, and procedures presented herein without departing from the scope or intention of the protocol. The recombinant DNA techniques employed are familiar to those skilled in the art of manipulating and cloning DNA fragments and employed persuant to the teachings of Sambrook et al.

Identification of a Differentially Expressed cDNA

A cDNA library derived from receptacle tissue mRNA is prepared in bacteriophage according to protocols well known to those skilled in the art. Kits and protocols for packaging DNA into bacteriophage are commercially available from sources such as Stratagene Cloning Systems (La Jolla, Calif.) and Gibco BRL (Gaithersburg, Md.). Bacteriophage are spread onto plates containing lawns of bacteria, preferably *Escherichia coli*, and most preferably *Escherichia coli* strain C600, to generate bacteriophage plaques. Between 100,000 and 1,000,000 plaques are made, more preferably between 200,000 and 500,000 plaques. Plaques are lifted onto DNA binding membranes, preferably nitrocellulose membranes. Two membrane lifts are made per plate of bacteriophage plaques. The pairs of membranes are probed to determine differential expression between receptacle tissue, and a non-receptacle tissue, preferably leaf. Probes are generated from mRNA isolated from the two chosen tissues. Probes may be radiolabeled, fluorescent, contain a conjugated enzyme for chemiluminescent detection, or possess some other means to facilitate detection. The synthesis of probes from mRNA is a skill well known to those in the art. Each pair of membranes is probed, the first membrane probed with receptacle tissue derived probes, and the second membrane probed with leaf or other non-receptacle tissue derived probes. After hybridization and development, the pairs of membranes are compared. Plaques which hybridize to the receptacle tissue derived probes, but not to the leaf or other tissue derived probes, display differential expression in receptacle tissue and are selected for further analysis.

Preparation of a Library of Genomic Fragments Cloned into Phage

Genomic DNA of a chosen species is partially digested with a restriction enzyme, preferably a restriction enzyme generating cohesive terminii, and more preferably restriction enzyme MboI. Digestion is allowed to proceed, with aliquots removed at discrete time intervals, preferably after each minute. Aliquots are analyzed by agarose gel electrophoresis to determine the degree of DNA cleavage. An aliquot containing DNA fragments of preferably between 14 kb and 23 kb in size is selected. A new sample of genomic DNA is digested with the same chosen restriction enzyme for the amount of time corresponding to the optimized aliquot. The digested DNA is fractionated by agarose gel electrophoresis, and DNA fragments between 14 kb and 23 kb are electrophoresed onto a piece of DEAE membrane. The membrane is washed in an aqueous solution containing approximately 150 mM NaCl, 20 mM Tris pH=8.0, and 0.1 mM EDTA. The membrane is transferred to a microcentrifuge tube, and a solution containing approximately 1.0 M NaCl, 20 mM Tris pH=8.0, 0.1 mM EDTA is added. The tube is heated, preferably at about 55° C. for approximately 25 minutes. The liquid containing eluted DNA is transferred to a new microcentrifuge tube, and lambda DASH phage arms, commercially available from Stratagene Cloning Systems (La Jolla, Calif.), or an equivalent, is added. Alcohol, preferably ethanol or isopropanol is added and the solution mixed to precipitate the DNA. The solution is cooled, preferably to −80° C. for about 1 hour. The DNA is pelleted by centrifugation, the liquid carefully removed, and the pellet rinsed carefully with approximately 70% ethanol chilled to about −20° C. The DNA is treated with DNA ligase under conditions as recommended by the enzyme manufacturer. Incubation is allowed to proceed at low temperature for greater than 12 hours, and preferably at 14° C. for 20 hours to ligate the lambda phage arms to the cleaved genomic DNA Packaging and Plating the Ligated Genomic DNA The ligated DNA is packaged into bacteriophage according to protocols well known to those skilled in the art. Kits and protocols for packaging DNA into bacteriophage are commercially available from sources such as Stratagene Cloning Systems (La Jolla, Calif.) and Gibco BRL (Gaithersburg, Md.). Bacteria, preferably *Escherichia coli*, and more preferably *Escherichia coli* strain C600 is used as the host organism for phage replication. Phage are plated onto lawns of bacteria to generate phage plaques. Preferably, about one million plaque forming units will be plated on a total of about 20 15 cm diameter petri plates. Plaques are lifted onto a DNA binding membrane, preferably a nitrocellulose membrane.

Identification of a Homologous Gene from the Genomic Library

Radiolabeled probes are synthesized from the selected cDNA fragments, and are used to screen the genomic library. Probes may be prepared by methods well known to those of skill in the art, as taught by Maniatas et al. cDNA obtained from *Fragaria X ananassa* or other plant species, or PCR fragments obtained therefrom may be used to probe the genomic DNA library.

If a cDNA from *Fragaria X ananassa* is used to probe the genomic library, hybridization should be performed under stringent conditions, preferably at about 65° C. After hybridization, the membranes should be washed for about 1 hour in 2× SSC buffer at about 65° C., then for about 30 minutes in 0.2× SSC buffer at about 65° C. before the membranes are used to expose X-ray film. More stringent hybridization and wash conditions are possible when using a cDNA probe from the same species as the genomic library.

If the probe cDNA or PCR fragment is derived from a species other than that used to create the genomic library, i.e. *Fragaria X ananassa*, hybridization should be performed at a lower temperature than 65° C., preferably about 45° C.

Bacteriophage DNA that hybridize to the labeled probe are selected for further analysis.

Cloning the Promoter Region from Identified Phage

Selected bacteriophage plaques are used to grow cultures of bacteriophage containing DNA capable of hybridizing to the probe sequence. Bacteriophage are incubated with a saturated overnight culture of bacteria to replicate. Incubation is allowed to proceed until the culture becomes visibly clear. Chloroform is added and incubation allowed to continue, preferably at 37° C. for 15 minutes. The resulting lysate is transferred to a centrifuge tube. Cell debris is pelleted by centrifugation, and the cleared aqueous lysate is transferred to a clean tube. DNAse and RNAse enzymes are added, and the lysate is incubated at 22° C. for 30 minutes, followed by the addition of polyethylene glycol and NaCl to a final concentration of 10% and 1 M, respectively. The solution is incubated at low temperature, preferably overnight at about 0° C. The solution is centrifuged, the supernatant removed, and the pellet allowed to air dry. The pellet is dissolved in SM buffer (50 mM tris-HCl pH=7.5, 8 mM $MgSO_4$, 100 mM NaCl, and 0.01% gelatin) and extracted with chloroform to remove residual polyethylene glycol and the aqueous phase is removed to a clean tube. Diethylpyrocarbonate, sodium dodecyl sulfate, and a tris hydrochloride buffer are added, and the mixture heated, preferably at about 70° C. for approximately 10 minutes. The tube is allowed to cool to room temperature, and an acetate salt, preferably potassium acetate, is added to facilitate precipitation of the DNA. The solution is incubated at about 0° C. for approximately 30 minutes. The liquid is centrifuged twice, and transferred to a new tube after each centrifugation. The DNA is precipitated with an alcohol, preferably ethanol or isopropanol. The DNA is pelleted by centrifugation, and the pellet is washed with 80% ethanol. The pellet is allowed to air dry. TE buffer is added to dissolve the DNA. The DNA is precipitated with an acetate salt and an alcohol, preferably sodium acetate and ethanol. The DNA is pelleted by centrifugation, washed with 80% ethanol, and allowed to air dry. RNAse and TE buffer are added to digest residual RNA.

Identification by Southern Hybridization of a Genomic Restriction Fragment Likely to Contain the Gene Promoter The isolated phage DNA is digested separately with a plurality of restriction enzymes, preferably six, and most preferably restriction enzymes EcoRI, HindIII, BamHI, PstI, XbaI, and SalI. The digested DNA is fractionated by agarose gel electrophoresis and immobilized onto a membrane, preferably a nylon membrane. Hybridization is performed as described above, with a labeled DNA fragment encompassing the 5' end of the cDNA, with the size of the fragment preferably between 0.3 kb and 1.0 kb in length.

Using this procedure it is possible to identify a restriction fragment between 1 and 10 kb in size which hybridizes to the desired coding sequence. A fragment of this size will likely also contain the region adjacent to the 5' end of the coding sequence constituting the promoter to this region.
Cloning the Genomic Fragment Likely to Contain the Desired Promoter into E. coli The restriction digest which produced the restriction fragment between 1 and 10 kb in size which hybridized to the probe is repeated. The fragment is isolated from an agarose gel using a DEAE cellulose membrane as described above, except that no phage DNA is added before alcohol precipitation. The DNA is dissolved in water.

A plasmid containing an antibiotic resistance marker and a β-galactosidase gene, preferably plasmid pUC119 DNA, is digested with the same restriction enzyme used to isolate the fragment above under the same conditions. Following digestion, a phosphatase enzyme, preferably calf intestinal alkaline phosphatase or shrimp alkaline phosphatase is added. Incubation is allowed to proceed, preferably at about 37° C. for approximately 30 minutes. An acetate salt and alcohol, preferably sodium acetate and ethanol, are added to facilitate precipitation. The mixture is cooled on dry ice, and centrifuged to pellet the DNA. The supernatant is removed, and the pellet is washed with 80% ethanol and allowed to air dry. The precipitated DNA is dissolved in water.

The digested plasmid and genomic DNA fragment are combined with a ligase enzyme, preferably T4 DNA ligase. The solution is incubated overnight at about 14° C. The DNA is transformed into a bacterial strain, preferably *Escherichia coli* strain JM101, by methods well known to those skilled in the art such as those methods described in Maniatas et al. Transformation methods can include, but are not limited to, calcium chloride, electroporation, and polyethylene glycol procedures. The transformed bacteria are spread onto a media plate containing an appropriate antibiotic for selection, and X-gal (5-bromo-4-chloro-3-indoyl-β-D-galactoside) for visual identification of transformants containing the desired insert. The presence of an insert in the plasmid disrupts the β-galactosidase reading frame, making the plasmid unable to encode a functional β-galactosidase enzyme that hydrolyzes X-gal to form a blue precipitate. Non-blue colonies should therefore contain the desired plasmid construct. Individual colonies are selected and grown in small scale liquid cultures, and their plasmid DNA harvested and digested with corresponding restriction enzymes to identify constructs containing the desired genomic DNA fragment.
Identifying the Promoter-Leader/Coding Sequence Digestion of the plasmid DNA with various restriction enzymes followed by Southern blotting allows the identification of a small restriction fragment, preferably 2 kb or less, which hybridizes to the 5' end of the isolated cDNA. This fragment is sequenced using a DNA sequencing kit, such as those commercially available from Amersham (Arlington Hights, Ill.), New England Biolabs (Beverly, Mass.), or any other preferred method. Comparison of the sequence obtained with the *Fragaria X ananassa* gene or the homologous cDNA (if available) should allow identification and orientation of the gene within the genomic fragment. This information is used to determine where the promoter-leader/coding sequence junction is located in the genomic fragment. If this sequence is not included, sequencing is continued using oligonucleotide primers made identical to the end of the previous sequence until the promoter-leader/coding sequence junction is obtained. Oligonucleotide primers may be ordered from commercial sources such as Oligos, etc. (Wilsonville, Oreg.) and Pharmacia (Piscataway, N.J.).

The size of the region 5' to the coding sequence in the isolated genomic fragment(s) should be determined from the location of the leader/coding sequence junction. If this region is less than 0.6 kb, it is necessary to isolate another genomic fragment containing a larger region upstream of the coding sequence, as a fragment of this size is unlikely to contain the entire promoter region. Genomic DNA hybridization with another phage DNA isolated from the differential screening is repeated until a genomic clone containing an upstream region of sufficient size is obtained.
Introducing a Convenient Restriction Site at the Promoter Leader/Coding Sequence Junction A synthetic oligonucleotide is designed that contains about 20 nucleotides of homology spanning the leader/coding sequence junction with a restriction enzyme recognition sequence inserted into the leader immediately adjacent to the start of the coding sequence. An enzyme recognition sequence is chosen that can be conveniently used to subclone a promoter-leader fragment at least 0.6 kb in size from the total genomic fragment, i.e. a restriction site that is not present in the promoter region. Plasmid DNA mutagenesis may be performed with kits commercially available from Bio-Rad (Hercules, Calif.), Stratagene Cloning Systems (La Jolla, Calif.) and New England Biolabs (Beverly, Mass.), or by any preferred protocol. Digestion of the putative mutated plasmid with the restriction enzyme corresponding to the inserted site facilitates identification of the desired plasmid.
Isolating the Promoter Region The mutagenized plasmid DNA is digested with restriction enzymes which release a promoter region fragment starting at the leader/coding sequence junction and extending at least 0.6 kb upstream from the structural gene sequence. This fragment may be isolated from agarose gel using DEAE cellulose as described earlier for the isolation of genomic DNA restriction fragments.

The isolated fragment may be utilized in a selected chimeric gene construction, cloned into any desired vector and transformed into plant cells to express a selected heterologous structural coding sequence in meristematic and/or rapidly dividing cells.

EXAMPLES

The following examples are provided to better illustrate the practice of the present invention and should not be interpreted in any way to limit the scope of the present invention. Those skilled in the art will recognize that various modifications, truncations, etcetera can be made to the methods and genes described herein while not departing from the spirit and scope of the present invention.

Example 1

Isolation and Sequencing of *Fragaria X ananassa* Promoters

A *Fragaria X ananassa* cDNA library was prepared from receptacle tissue in the lambda ZAP vector according to the protocol supplied by Stratagene Cloning Systems (La Jolla, Calif.). Greater than $1.3 \times 10^7$ recombinant plaques were obtained when phage were plated on a lawn of *Escherichia coli* strain XL1-Blue MRF'. More than 50,000 plaques were plated on a lawn of XL1-Blue cells and lifted onto nitrocellulose membranes, with two membrane lifts being made per plate of bacteria. Membranes were assayed individually with $^{32}$P labeled probes made from mRNA isolated from leaf and receptacle tissue using the random oligonucleotide primer method (Prime-it II kit, Stratagene Cloning Systems, La Jolla, Calif.). Plaques were identified whose DNA hybridized to probes made from receptacle tissue mRNA, but did not hybridize to probes made from leaf tissue. Greater than 150 plaques were so identified. Corresponding bacteriophage from 60 plaques were selected and excised by phagemid rescue and replicated in cultures of bacterial strain *Escherichia coli* SOLR. DNA was harvested, and the recombinant plasmids were screened by restriction digestion of the plasmids. Southern blot hybridization was performed using radiolobeled DNA probes from mRNA prepared from leaf and receptacle tissues as described above. The DNAs of plasmids that hybridized preferentially to receptacle radiolabeled probes and not to leaf radiolabeled probes were selected. Replica Southern blots of restriction digested cDNA clones were cross-hybridized to determine different/novel clones. Different, non-homologous cDNA clones were sequenced using the Sequenase kit (United States Biolabs, Cleveland, Ohio). Several sequences were so identified, of which two were selected and the coding sequences designated as SRE2 and SRE49. No sequence variability was observed between different plaque DNAs containing the same sequence. Northern RNA blots containing RNA from leaves, and different receptacle developmental stages: small green receptacles, white-red turning stage receptacles, full red receptacles, and over-ripe receptacles, were hybridized to cDNA inserts of SRE2 and SRE49. This lack of sequence variability suggested that the promoters and structural sequences are present at low copy numbers in the cellular DNA.

Two sequences were isolated by PCR with degenerate primers from beta, 1–4 glucanase (cellulase) sequences. Using cellulase degenerate primers (SEQ ID NO. 13. and SEQ ID NO. 14), reverse transcriptase PCR was conducted using mRNA isolated from ripening receptacles. PCR products were generated that corresponded to 255 bp, the predicted size expected based on the nucleotide distance between primers designed to the coding sequence of cellulase. The PCR products identified were gel purified and cloned into plasmid pBluescript. The plasmid DNAs of 60 clones were prepared and sequenced to verify their homology with cellulase, and to distinguish different family members. Six different sequences were identified from independent clones homologous to the known coding sequences of avocado, bean, tomato, and soybean. Inserts from clones containing different cellulase sequences were purified by restriction endonuclease digestion and agarose gel electrophoresis. Northern RNA blots containing RNA from leaves, and different receptacle developmental stages: small green receptacles, white-red turning stage receptacles, full red receptacles, and over-ripe receptacles, were hybridized to cellulase cDNA inserts radiolabeled using the random primter labeling Prime-it II Kit (Stratagene Cloning Systems, La Jolla, Calif.). Four of the six PCR cDNA products were fruit enhanced and two, SEL1 and SEL2 were further selected for promoter isolation.

Once the *Fragaria X ananassa* cDNAs were identified, the cDNAs of SRE2 and SRE 49, and SEL1 and SEL2 were used to screen a *Fragaria X ananassa* Selva genomic library to identify the genomic equivalents. The cDNAs were radiolabeled as described previously and used to screen a *Fragaria X ananassa* genomic library constructed from leaf total genomic DNA. The genomic library was prepared in the lambda DASH vector as described by Stratagene Cloning Systems (La Jolla, Calif.). The library was screened for plaques hybridizing to the SRE2 and SRE49 cDNAs by plaque lift hybridization with the random primer labeled cDNA probes as described in the Prime-it random primer labeling kit (Stratagene Cloning Systems, La Jolla, Calif.). Several plaques containing *Fragaria X ananassa* genomic DNA hybridizing to the cDNAs were identified. The plaques were isolated and phage DNA isolated therefrom. Phage DNA segments homologous to the cDNA inserts were identified by restriction digestion and Southern blots. Hybridizing fragments were subcloned into plasmid pBluescript.

Example 2

Construction of GUS Reporter Systems to Assay Promoter Function in Plants

A 6.0 kb EcoRI genomic fragment containing the isolated SRE2 gene, hybridizing to probes made from SRE2 cDNA sequence, was isolated from phage DNA, and cloned into the EcoRI restriction site of plasmid pBluescript SK to create plasmid pGS2-4. A 6.2 kb EcoRI genomic fragment containing the isolated SRE49 gene, hybridizing to probes made from the SRE49 cDNA sequence, was isolated from phage DNAs and cloned into the EcoRI restriction site of plasmid pBluescript SK to create plasmids pGS49-4E and pGS49-4E1.5. The pGS2-4 and pGS49-4 clones were partially sequenced to identify predicted translational start sites and the 5' regulatory promoter sequences using primers derived from internal sequence of SRE2 and SRE49 cDNAs. NcoI and BglII restriction sites were then introduced into both pGS2-4 and pGS49-4 at the junction of the *Fragaria X ananassa* promoter-leader sequence and its corresponding coding sequence by site directed mutagenesis.

The oligonucleotide primer used for mutagenesis of plasmid pGS2-4 consisted of the following sequence: 5'-GTAAATCAATTCCG<u>AGATCT</u>ACCATG <u>G</u>CTGGAAAGT GCG-3' (SEQ ID NO. 9). The underlined nucleotides were used to create BglII and NcoI restriction sites. Site directed in vitro mutagenesis was performed using the Muta-gene mutagenesis system (Bio-Rad, Hercules, Calif.), as per the manufacturer's instructions. These mutations resulted in a 0.8 kb fragment that contained the promoter region and untranslated leader of the 6.0 kb EcoRI fragment that was isolated and subcloned from the genomic clone corresponding to the SRE2 cDNA. The CaMV35S promoter in the expression cassette of pMON8677 was replaced by the *Fragaria X ananassa* GSRE2 promoter by inserting the 0.8 kb BglII-NotI fragment from the mutagenized pGS2 plasmid into pMON8677 digested completely with BglII and partially with NotI to create plasmid pMON18328. The pMON18328 vector created in this example contains a chimeric gene consisting of the *Fragaria X ananassa* GSRE2 promoter, GUS coding sequence, and NOS 3'. Plasmid pMON18342 was combined with plasmid pMON18328 in Agrobacterium to afford transformation vector pMON18347 used to test the *Fragaria X ananassa* GSRE2 promoter in plants.

The oligonucleotide primer used for mutagenesis of pGS49-4 consisted of the sequence: 5'-TTAGACTGCTG <u>AGATCT</u>ACC<u>A</u>TGGTTACGTCTGTACTTG-3' (SEQ ID NO. 10). The underlined nucleotides are substitutions in the original sequence to create BglII and NcoI restriction sites. Site directed mutagenesis was performed using the Muta-gene mutagenesis system (Bio-Rad, Hercules, Calif.), as per the manufacturer's instructions. The mutations resulted in a 1.2 kb fragment that contained the promoter region and untranslated leader from the 1.5 kb EcoRI fragment isolated and subcloned from the genomic clone corresponding to the 5' end of the SRE49 cDNA. The resulting 1.2 kb NcoI-EcoRI fragment was used as the *Fragaria X ananassa* GSRE49 promoter and cloned into the NcoI-EcoRI restriction sites replacing the GSRE2 promoter of pMON18328 to create pMON18337. The pMON18337 vector created in this example contains a chimeric gene consisting of the *Fragaria X ananassa* GSRE49 promoter, GUS coding sequence, and NOS 3'. Plasmid pMON18342 was combined with plasmid pMON18337 in Agrobacterium to afford transformation vector pMON18354 used to test the *Fragaria X ananassa* GSRE49 promoter in plants.

An 8.0 kb XbaI genomic fragment containing the SEL1 gene was identified and isolated from phage DNA as described above. The fragment was cloned into the XbaI restriction site of plasmid pBluescript SK. An NcoI restriction site was introduced into this fragment using site directed mutagenesis with an oligonucleotide primer homologous to the translational start site consisting of the following sequence: 5'-ACGAGAGAGA GAGAAAA CCATGGCGCGAAATGGCC-3' (SEQ ID NO. 11). The underlined sequences were inserted to create the NcoI restriction site. Site directed mutagenesis was performed using the Mutagene system (Bio-Rad, Hercules, Calif.), as per the manufacturer's instructions, and resulted in a 2.0 kb promoter-leader fragment. This 2.0 kb NotI-NcoI fragment was then inserted into the XbaI and NcoI restriction sites of pMON18328 replacing the GSRE2 promoter, creating pMON18355. The resulting vector created in this example contains a chimeric gene consisting of the *Fragaria X ananassa* SEL1 promoter, GUS coding sequence and NOS 3' end. Plasmid pMON18355 was combined with plasmid pMON18355 in Agrobacterium to afford transformation vector pMON18356 used to test the *Fragaria X ananassa* SEL1 promoter in plants.

A 6.0 kb EcoRI-SacII fragment containing the SEL2 gene was identified and isolated from phage DNA as described above. This fragment was cloned into the EcoRI and SacII restriction sites of plasmid pBluescript SK. An NcoI restriction site was introduced by site directed mutagenesis using an oligonucleotide primer consisting of the following sequence: 5'-CACAAATTTCTCCATGGTGGATC CCTGGTCATATC-3' (SEQ ID NO. 12). The underlined sequences were inserted to create the NcoI and BamHI restriction sites. Site directed mutagenesis was performed using the Mutagene system (Bio-Rad, Hercules, Calif.), as per the manufacturer's instructions. The SEL2 promoter was digested with EcoRI and the overhang was filled using Klenow fragment of DNA polymerase I, and then digested with NcoI. The resulting 4.5 kb NcoI-blunt filled EcoRI fragment contained the SEL2 promoter-leader and was inserted into HindIII and NcoI digested pMON10018 replacing the FMV promoter by blunting the HindIII restriction site as described above creating pMON18357. The resulting vector created in this example contains a chimeric gene consisting of the *Fragaria X ananassa* SEL2 promoter, GUS coding sequence and NOS 3' end. Plasmid pMON18342 was combined with plasmid pMON18357 in Agrobacterium to afford transformation vector pMON18358 used to test the *Fragaria X ananassa* SEL1 promoter in plants.

Example 3

Plant Assay of Promoter-GUS Chimeric Gene Expression

The promoters fused to the GUS gene were transformed into tomato and tobacco using Agrobacterium-mediated transformation techniques well known to those of skill in the art. β-glucuronidase (GUS) expression was observed by histochemical staining of hand sectioned fruit (tomato) or seed (tobacco). More specifically, four strawberry promoter-β-glucuronidase fusion constructs have been examined in both tomato and tobacco (Klee, H. J. et al. (1985) Bio/Technology 3:637–642; Horsch, R. B. and H. J. Klee (1986) PNAS U.S.A. 83:4428–4432. Rogers, S. G. et al. (1987) "Improved Vectors for Plant Transformation: Expression Cassette Vectors and New Selectable Markers" in Methods in Enzymology, ed. Wu and Grossman, pp253–277, San Diego: Academic Press.

pMON18347: GSRE2/GUS/NOS

Tobacco: GUS activity (staining) was observed primarily in the peduncle, and floral receptacle, and continuing through the inner tissues of the ovary; staining at early stages of seed development was not detected.

Tomato: GUS activity was detected throughout immature green fruit; leaf expression of the GUS gene was not detected by staining.

pMON18354: GSRE49/GUS/NOS

Tobacco: GUS activity (staining) was observed primarily in the peduncle, and floral receptacle, and continuing through the inner tissues of the ovary; staining at early stages of seed developments was not detected.

Tomato: GUS activity was very low in lines generated from this construct.

pMON18356: SEL1/GUS/NOS

Tobacco: GUS activity (staining) was observed primarily in the floral receptacle and ovary tissues, and during immature stages of seed development.

Tomato: GUS activity was detected throughout immature green fruit; expression was not detectable by staining of leaf tissue.

pMON18358: SEL2/GUS/NOS

Tobacco: GUS activity was observed primarily in the floral receptacle and ovary tissues; staining at early stages of seed development was not detected.

Tomato: GUS activity was detected throughout immature green fruit; with weak expression in the pericarp; expression was not detectable by staining of leaf tissue.

Table 1 shows the differential expression of GUS under control of the four disclosed promoters in tobacco plants and seeds. Table 2 demonstrates the differential expression of GUS under control of the four disclosed promoters in tomato plants. In all cases, no detectable GUS activity was observed in leaf tissue. These results confirm the utility of the disclosed promoters in the differential expression of sequences in plant tissues.

TABLE 1

Summary of GUS activity detected in tobacco R0 plants and R1 seed

| Construct | Leaf | peduncle | Floral base | Ovary | Immature seed* |
|---|---|---|---|---|---|
| 18347 (31) | − | | + | ++ | − |
| 18354 (35) | − | | + | ++ | − |
| 18356 (30) | − | | +/− | ++ | + |
| 18358 (36) | − | | +/− | +/− | − |

*only a few lines from each of the constructs were assayed for immature seed expression Numbers in parenthesis indicate number of positive independent lines assayed.

TABLE 2

Summary of GUS activity detected in tomato R0 plant

| Construct | Leaf* | Placenta | Columnella | Pericarp |
|---|---|---|---|---|
| 18347 (13) | − | + | + | + |
| 18354 (4) | − | +/− | + | +/− |
| 18356 (19) | − | + | + | +/− |
| 18358 (15) | − | + | + | +/− |

*only a few lines from each of the constructs were assayed for leaf expression. Numbers in parenthesis indicate number of positive independent lines assayed.

Example 4

Expression of Glucose Oxidase in Strawberries

Strawberry plants were transformed with plasmid pMON18349 (GSRE2 AGO nos3'). This construct places the *Aspergillus niger* glucose oxidase sequence (GenBank Accession No. J05242) under control of the GSRE2 promoter.

Twenty-three transgenic strawberry lines which produced glucose oxidase protein in ripe fruit were analyzed. Expression levels of glucose oxidase protein in various tissues including fruit, young and old leaves, stems, roots, runner, and flowers were examined by Western blot analysis (for general information, see Towbin, H., et al. *Proc. Natl. Acad. Sci. U.S.A.* 76: 4350, 1979; Burnette, W. N. *Anal. Biochem.* 112: 195, 1981) and ELISA (Methods in Molecular Biology, vol. 10, Immunochemical Protocols, edited by Margaret M. Manson, 1992, Humana Press, Inc., Totowa, N.J.). Glucose oxidase protein was not detectable in leaf, stem, root, and flower tissues in the majority of the transgenic lines, indicating that the GSRE2 promoter is fruit specific or fruit enhanced. The expression data in fruit and flower tissues as determined by ELISA analysis is shown in Table 3. Glucose oxidase protein in plant tissue was determined by ELISA using specific antibodies against *A. niger* glucose oxidase.

TABLE 3

Accumulation of glucose oxidase protein in fruit and flower tissues

| | Amount of Glucose oxidase protein (ng/g fresh weight) | | |
|---|---|---|---|
| Transgenic line | Fruit | Flower bud[a] | Petal |
| Redcoat (control) | 0 | 0 | 0 |
| 116-3 | 26.24 | 0 | 0 |
| 116-5 | 45.22 | 36.20 | 0 |
| 144-3 | 55.20 | 0 | 0 |
| 144-4 | 10.40 | 0 | 0 |
| 144-5 | 63.84 | 0 | 0 |
| 148-1 | 25.76 | 0 | 0 |
| 148-2 | 16.50 | 0 | 76.12 |
| 148-3 | 76.64 | 0 | 312.00 |
| 148-4 | 62.40 | 25.20 | 288.00 |
| 149-2 | 7.28 | 0 | 0 |
| 154-1 | 40.80 | 0 | 0 |
| 154-3 | 28.64 | 0 | 0 |
| 154-4 | 22.88 | 0 | 0 |
| 154-5 | 34.56 | 0 | 0 |
| 164-3 | 12.32 | 0 | 0 |
| 164-4 | 21.26 | 0 | 0 |
| 164-6 | 20.06 | 0 | 0 |
| 168-1 | 2.88 | 0 | 0 |
| 168-2 | 42.08 | 0 | 0 |
| 168-4 | 9.12 | 0 | 0 |
| 170-1 | 36.54 | 0 | 0 |
| 170-3 | 36.00 | 0 | 0 |
| 170-8 | 26.24 | 0 | 0 |
| 172-1 | 16.14 | 0 | 0 |
| 172-2 | 22.54 | 0 | 0 |
| 172-3 | 32.60 | 0 | 0 |
| 172-4 | 20.11 | 0 | 0 |

[a]Flower bud represents the remaining of a young flower with petals removed.

While the compositions and methods of this invention have been described in terms of preferred embodiments, it will be apparent to those of skill in the art that variations may be applied to the processes described herein without departing from the concept, spirit and scope of the invention. All such similar substitutes and modifications apparent to those skilled in the art are deemed to be within the spirit, scope and concept of the invention.

REFERENCES

The following references, to the extent that they provide exemplary procedural or other details supplementary to those set forth herein, are specifically incorporated herein by reference.

Bevan, M., et al., *Nature*, 304: 184 (1983).
Coruzzi, G., Broglie, R., Edwards, C., Chua, N. H., *EMBO J.*, 3: 1671 (1984).
Deikman, J., et al., *EMBO J.*, 7: 3315–3320 (1988).
Ditta, G., et al., *Proc. Natl. Acad. Sci. U.S.A.*, 77: 7347–7351 (1980).
Feinberg, A., et al., *Anal. Biochem.*, 132: 6 (1983).
Feinberg, A. and Vogelstein, B., *Anal. Biochem.* 137: 266 (1984).
Fraley, R. T., Rogers, S. G., Horsch, R. B., Eichholtz, D. A., Flick, J. S., Fink, C. L., Hoffmann, N. L. and Sanders, P. R., *Bio/Technology*, 3: 629–635 (1985).
Fraley, R. T., et al., *Proc. Natl. Acad. Sci. U.S.A.*, 80: 4803 (1983).
Fry, J., Barnason, A. and Horsch, R., *Plant Cell Reports*, 6: 321325 (1987).
Gasser, C. S., Winter, J. A., Hironaka, C. M. and Shah, D. M., *J. Biol. Chem.*, 263: 4280–4289 (1988).
Gasser, C. S., Budelier, K. A., Smith, A. G., Shah, D. M. and Fraley, R. T., *Plant Cell*, 1: 15–24 (1989).
Hayford, M., et al., *Plant Physiol.*, 86: 1216–1222 (1988).
Herrera-Estrella, L., et al., *Nature*, 303: 209 (1983).
Horsch R. and Jones, G., *In Vitro*, 16: 103–108 (1980).
Horsch R., Fry J., Hoffman, N., Wallworth, M., Eicholtz, D., Rogers, S., and Fraley, R., *Science*, 227: 1229–1231 (1985).
Horsch, R. B. and Klee, H. *Proc. Natl. Acad. Sci. U.S.A.*, 83: 4428–32 (1986).
James, A. *Plant Sci.*, 69: 79–94 (1990).
Jefferson, R. A., Kavanagh, T. A. and Bevan, M. W., *EMBO J.*, 6: 3901–3907 (1987).
Kay, R., Chan, A., Daly, M., McPherson, J., *Science*, 236: 12991302 (1987).
Klee, H., et al., *Bio/Technology*, 3: 637–642 (1985).
Lin, et al., Plant Mol. Biol. 23: 489–499 (1993)
Maniatis, T., Fritsch, E. F. and Sambrook, J. *Molecular Cloning*, pp. 320–322, Cold Spring Harbor Laboratory (1982).

Morelli, G., Nagy, F., Fraley, R. T., Rogers, S. G., Chua, N. H., *Nature*, 315: 200–204 (1985).

Rochester, D. E., Winter, J. A. and Shah, D. M. *EMBO J.*, 5: 451458 (1986).

Rogers, S. G., et al., *Methods in Enzymology*, ed. Wu and Grossman, pp 253–277, San Diego: Academic Press (1987).

Sanger, F., et al., *Proc. Natl. Acad. Sci. U.S.A.*, 4: 5463–5467 (1977).

Schmidhauser, T. J. and Helinski, D. R., *J. Bateriol.* 164–155 (1985)

Stringam, G. R., *Plant Science Letter*, 9: 115–119 (1977).

Theologis, A., *Cell*, 70: 181–184 (1992).

Young, R. A. and Davis, R. W., *Proc. Natl. Acad. Sci. U.S.A.*, 80: 1194–1198 (1983).

---

What is claimed is:

1. An isolated plant promoter comprising SEQ ID NO:1.
2. An isolated plant promoter comprising SEQ ID NO:2.
3. An isolated plant promoter comprising SEQ ID NO:3.
4. An isolated plant promoter comprising SEQ ID NO:4.
5. A chimeric gene comprising operably linked in the 5' to 3' direction:
   a) a promoter functional to direct transcription of a structural DNA coding sequence in receptacle fruit tissue, wherein said promoter effects higher levels of transcription in receptacle fruit tissue than in non-fruit tissue, wherein the promoter comprises SEQ ID NO: 1, SEQ ID NO:2, SEQ ID NO:3, or SEQ ID NO:4; and
   b) a structural DNA coding sequence heterologous to said promoter.
6. The chimeric gene of claim 5, wherein said structural DNA coding sequence encodes glucose-6-phosphatase, sucrose phosphate synthase, ACC synthase, ACC deaminase, sucrose synthase, or invertase.
7. A genetically transformed plant cell comprising operably linked in the 5' to 3' direction:
   a) a promoter functional to direct transcription of a structural DNA coding sequence in receptacle fruit tissue, wherein said promoter effects higher levels of transcription in receptacle fruit tissue than in non-fruit tissue, wherein the promoter comprises SEQ ID NO:1, SEQ ID NO:2, SEQ ID NO:3, or SEQ ID NO:4,
   b) a structural DNA coding sequence heterologous to said promoter; and
   c) a 3' polyadenylation signal sequence that directs the addition of polyadenylate nucleotides to the 3' end of RNA transcribed from said structural DNA coding sequence.
8. A plant comprising the plant cell of claim 7.
9. The plant of claim 8, further defined as a strawberry, raspberry, tomato, potato, tobacco, soybean, or cotton plant.

10. A method of producing a protein in plants or plant cells, the method comprising:
   transforming plants or plant cells with a chimeric gene comprising operatively linked in the 5' to 3' direction:
      a) a promoter functional to direct transcription of a structural DNA coding sequence in receptacle fruit tissue, wherein said promoter effects higher levels of transcription in receptacle fruit tissue than in non-fruit tissue, wherein the promoter comprises SEQ ID NO:1, SEQ ID NO:2, SEQ ID NO:3, or SEQ ID NO:4;
      b) a structural DNA coding sequence heterologous to said promoter, wherein the structural DNA coding sequence encodes said protein; and
      c) a 3' polyadenylation signal sequence that directs the addition of polyadenylate nucleotides to the 3' end of RNA transcribed from said structural DNA coding sequence.
11. A method of producing an antisense RNA sequence in plant cells or plants, said method comprising:
   transforming plant cells or plants with a chimeric gene comprising in operable linkage:
      a) a promoter functional to direct transcription of an antisense DNA sequence in receptacle fruit tissue, wherein said promoter effects higher levels of transcription in receptacle fruit tissue than in non-fruit tissue, wherein the promoter comprises SEQ ID NO: 1, SEQ ID NO:2, SEQ ID NO:3, or SEQ ID NO:4; and
      b) an antisense DNA sequence encoding said antisense RNA sequence, wherein said antisense DNA sequence is complementary to a structural DNA coding sequence.
12. The method of claim 11, wherein said structural DNA coding sequence is a glucose-6-phosphate structural DNA coding sequence.

* * * * *

UNITED STATES PATENT AND TRADEMARK OFFICE
CERTIFICATE OF CORRECTION

PATENT NO. : 6,080,914
DATED : June 27, 2000
INVENTOR(S) : Conner

It is certified that error appears in the above-identified patent and that said Letters Patent is hereby corrected as shown below:

<u>Claim 12, column 34,</u>
Line 45, delete "phosphate" and replace with -- phosphatase --.

Signed and Sealed this

Eighteenth Day of September, 2001

Attest:

*Nicholas P. Godici*

NICHOLAS P. GODICI
*Attesting Officer*    *Acting Director of the United States Patent and Trademark Office*